United States Patent [19]
Keith et al.

[11] Patent Number: 5,522,818
[45] Date of Patent: Jun. 4, 1996

[54] BALLOON CATHETER WITH DISTAL GUIDE WIRE LUMEN

[75] Inventors: Peter T. Keith, Fridley; Charles L. Euteneuer, St. Michael, both of Minn.

[73] Assignee: SciMed Life Systems, Inc., Maple Grove, Minn.

[21] Appl. No.: 521,460

[22] Filed: Aug. 30, 1995

Related U.S. Application Data

[63] Continuation of Ser. No. 344,931, Nov. 23, 1994, abandoned, which is a continuation of Ser. No. 35,254, Mar. 22, 1993, Pat. No. 5,395,334, which is a continuation of Ser. No. 792,786, Nov. 15, 1991, Pat. No. 5,217,482, which is a continuation of Ser. No. 574,265, Aug. 28, 1990, Pat. No. 5,156,594.

[51] Int. Cl.[6] .......................... A61M 29/00; A61M 25/00
[52] U.S. Cl. .......................... 604/102; 604/282; 606/194
[58] Field of Search ........................ 604/96–103, 280, 604/282; 606/192–196; 600/18; 128/207.15

[56] References Cited

U.S. PATENT DOCUMENTS

| 2,687,131 | 8/1954 | Raiche . |
| 2,936,760 | 5/1960 | Gants . |
| 3,225,762 | 12/1965 | Guttman . |
| 4,289,128 | 9/1981 | Rüsch .................... 128/207.15 |
| 4,468,224 | 8/1984 | Enzmann et al. ............ 604/247 |
| 4,597,755 | 7/1986 | Samson et al. ............. 604/96 |
| 4,662,368 | 5/1987 | Hussein et al. . |
| 4,705,507 | 11/1987 | Boyles ...................... 604/101 |
| 4,748,982 | 6/1988 | Horzewski et al. . |
| 4,762,129 | 8/1988 | Bonzel . |
| 4,771,777 | 9/1988 | Horzewski et al. . |
| 4,798,598 | 1/1989 | Bonello et al. ............. 604/280 |
| 4,820,349 | 4/1989 | Saab . |

(List continued on next page.)

FOREIGN PATENT DOCUMENTS

| 0344530A1 | 12/1989 | European Pat. Off. . |
| 0365993A1 | 5/1990 | European Pat. Off. . |
| 0368523A2 | 5/1990 | European Pat. Off. . |
| 0380873B1 | 5/1990 | European Pat. Off. . |
| 0380873A3 | 8/1990 | European Pat. Off. . |
| 0380873A2 | 8/1990 | European Pat. Off. . |
| 1251-914-A | 8/1986 | U.S.S.R. . |
| 627828 | 10/1988 | U.S.S.R. . |

OTHER PUBLICATIONS

Declaration of Paul G. Yock, M.D., in Support of ACS's Opposition to Schneider's Motion for Preliminary Injunction, dated Nov. 27, 1989, filed Dec. Dec. 4, 1989, in Schneider (Europe) AG v. Adavanced Cardiovascular Systems, Inc. No. C88–20742–WAI, United States District Court, Northern District of California (including Exhibits 1–7) made public on or date even with or prior to Aug. 28, 1990.

(List continued on next page.)

*Primary Examiner*—John D. Yasko
*Assistant Examiner*—Adam J. Cermak
*Attorney, Agent, or Firm*—Nawrocki, Rooney & Sivertson

[57] ABSTRACT

An over-the-wire balloon dilatation catheter has a stainless steel hypotube catheter shaft, an intermediate sleeve section bonded to the shaft and a distal balloon section connected to the sleeve section. The sleeve section is formed from relatively flexible polymer materials and includes an inner core tube which defines a guide wire lumen extending only through a distal portion of the catheter (including its sleeve and balloon sections) to facilitate fast balloon catheter exchanges. A distal end of the hypotube shaft is crimped laterally and the core tube is nested and bonded within the crimp to provide a proximal outlet for the guide wire lumen. The hypotube shaft provides an inflation lumen for the balloon, with the inflation lumen being continued as an annular inflation lumen through the sleeve section where an outer sleeve is bonded about the core tube and extends from the distal end of the hypotube shaft to the balloon section. A kink-resistant coil structure extends distally from the distal end of the hypotube shaft to provide a gradual change in stiffness along the length of the catheter from the relatively stiff hypotube shaft to the relatively flexible distal portion of the catheter.

11 Claims, 6 Drawing Sheets

U.S. PATENT DOCUMENTS

| | | | |
|---|---|---|---|
| 4,824,435 | 4/1989 | Giesy et al. | 604/49 |
| 4,838,268 | 6/1989 | Keith et al. | |
| 4,846,174 | 7/1989 | Willard et al. | |
| 4,877,031 | 10/1989 | Conway et al. | |
| 4,881,547 | 11/1989 | Danforth | |
| 4,896,670 | 1/1990 | Crittenden | 606/194 |
| 4,906,241 | 3/1990 | Noddin et al. | 606/194 |
| 4,917,088 | 4/1990 | Crittenden | 606/194 |
| 4,921,478 | 5/1990 | Solano et al. | 604/53 |
| 4,928,693 | 5/1990 | Goodin et al. | 128/637 |
| 4,940,062 | 7/1990 | Hampton et al. | 128/772 |
| 4,943,278 | 7/1990 | Euteneuer et al. | 604/96 |
| 4,944,745 | 7/1990 | Sogard et al. | 606/194 |
| 4,946,466 | 8/1990 | Pinchuk et al. | 606/194 |
| 4,953,553 | 9/1990 | Tremulis | 128/637 |
| 4,976,690 | 12/1990 | Solar et al. | 604/96 |
| 4,976,720 | 12/1990 | Machold et al. | 606/194 |
| 4,988,356 | 1/1991 | Crittenden et al. | 606/192 |
| 4,994,032 | 2/1991 | Sugiyama et al. | 604/96 |
| 4,998,917 | 3/1991 | Gaiser et al. | 604/96 |
| 4,998,923 | 3/1991 | Samson et al. | 606/194 |
| 5,032,113 | 7/1991 | Burns | 604/96 |
| 5,034,001 | 7/1991 | Garrison et al. | 604/53 |
| 5,035,686 | 7/1991 | Crittenden et al. | 604/96 |
| 5,035,705 | 7/1991 | Burns | 606/194 |
| 5,040,548 | 8/1991 | Yock | |
| 5,042,985 | 8/1991 | Elliot et al. | 606/192 |
| 5,047,045 | 9/1991 | Arney et al. | 606/194 |
| 5,050,606 | 9/1991 | Tremulis | 128/637 |
| 5,057,120 | 10/1991 | Farcot | 606/194 |
| 5,061,273 | 10/1991 | Yock | 606/194 |
| 5,102,390 | 4/1992 | Crittenden et al. | 604/96 |
| 5,102,403 | 4/1992 | Alt | 604/280 |
| 5,169,386 | 12/1992 | Becker et al. | 604/49 |
| 5,176,637 | 1/1993 | Sagae | 604/96 |
| 5,180,367 | 1/1993 | Kontos et al. | 604/101 |

OTHER PUBLICATIONS

"USCI Lo Profile II Balloon Dilatation Catheters," C. R. Card, Inc. 1987.

"Until Someone Does It, No One Thinks It Can Be Done," C. R. Bard, Inc., 1988.

Schneider–Shiley, brochure entitled *Monorail–Bonzel Coronary Dilatation System*, published on date even with or prior to Nov. 23, 1994.

*Monorail–Piccolino*, Flyer, Oct., 1988.

*ACS RX*™ *Dilatation Catheters*, Flyer, Mar., 1989.

*Balloon Catheters for Percutaneous Insertion Into the Vascular System*, Björn Nordenström, Mar. 2, 1962.

"New Instruments for Catheterization and Angiocardiography," Björn Nordenström, Jul.–Dec. 1965 Issue of *Radiology*.

Paul G. Yock, U.S. Patent Application Ser. No. 852,197, Filed Apr. 15, 1986, published Jun. 1988 in U.S.P.N. 4,748,982.

Exhibit 1 to Yock Declaration dated Dec. 4, 1989: Curriculum Vitae of Paul G. Yock, M.D., 5 pages.

Exhibit 2 to Yock Declaration dated Dec. 4, 1989: Written Description entitled "Single–Operator Angioplasty System", 5 pages.

Exhibit 3 to Yock Declaration dated Dec. 4, 1989: Copy of Slide Comparing the ACS RX® with the original Schneider Monorail®, 1 page.

Exhibit 4 to Yock Declaration dated Dec. 4, 1989: Ronald E. Vlietstra, M.B., Ch. B. et al., article entitled "PTCA Percutaneous Transluminal Coronary Angioplasty", 2 pages, Roger F. J. Shepherd, M.B., B. Ch. et al., article entitled "The History of Balloon Angioplasty", 3 pages.

Exhibit 5 to Yock Declaration dated Dec. 4, 1989: L. E. Afzelius et al., *Lakartidningen*, article entitled "Ballongdilatation Av Esofagusstrikturer En Ny Behandlingsmetod", vol. 79, No. 30–31 (1982), 3 pages, and English translation, 13 pages.

Exhibit 6 to Yock Declaration dated Dec. 4, 1989: Albert A. Moss, M.D. et al., *NMR, CT, and Interventional Radiology*, article entitled "Interventional Gastrointestinal Procedures", 8 pages.

Exhibit 7 to Yock Declaration dated Dec. 4, 1989: Copy of U.S. Pat. No. 3,884,242 entitled "Catheter Assembly" in the name of Bazell et al., 11 pages.

Declaration of Peter T. Keith with Exhibits A–D dated Oct. 9, 1995, 14 pages.

Exhibit A to the Keith Declaration dated Oct. 9, 1995: Schneider (USA) Inc., *Interventional Cardiology*, brochure entitled "Monorail–Piccolino Coronary Balloon Dilatation Catheters", dated Oct. 1988, 2 pages.

Exhibit B to the Keith Declaration dated Oct. 9, 1995: Schneider (USA) Inc. brochure entitled "A Message for Overachievers Everywhere" dated Jul. 1989, 5 pages.

Exhibit C to the Keith Declaration dated Oct. 9, 1995: Schneider (USA) Inc. brochure entitled "Monorail Piccolino® PICA Balloon Catheters", dated Jul. 1990, 1 page.

Exhibit D to the Keith Declaration dated Oct. 9, 1995: Schneider (USA) Inc. brochure entitled "The Next Generation PTCA Catheter Series for Overachievers Everywhere", dated Mar. 1990, 2 pages.

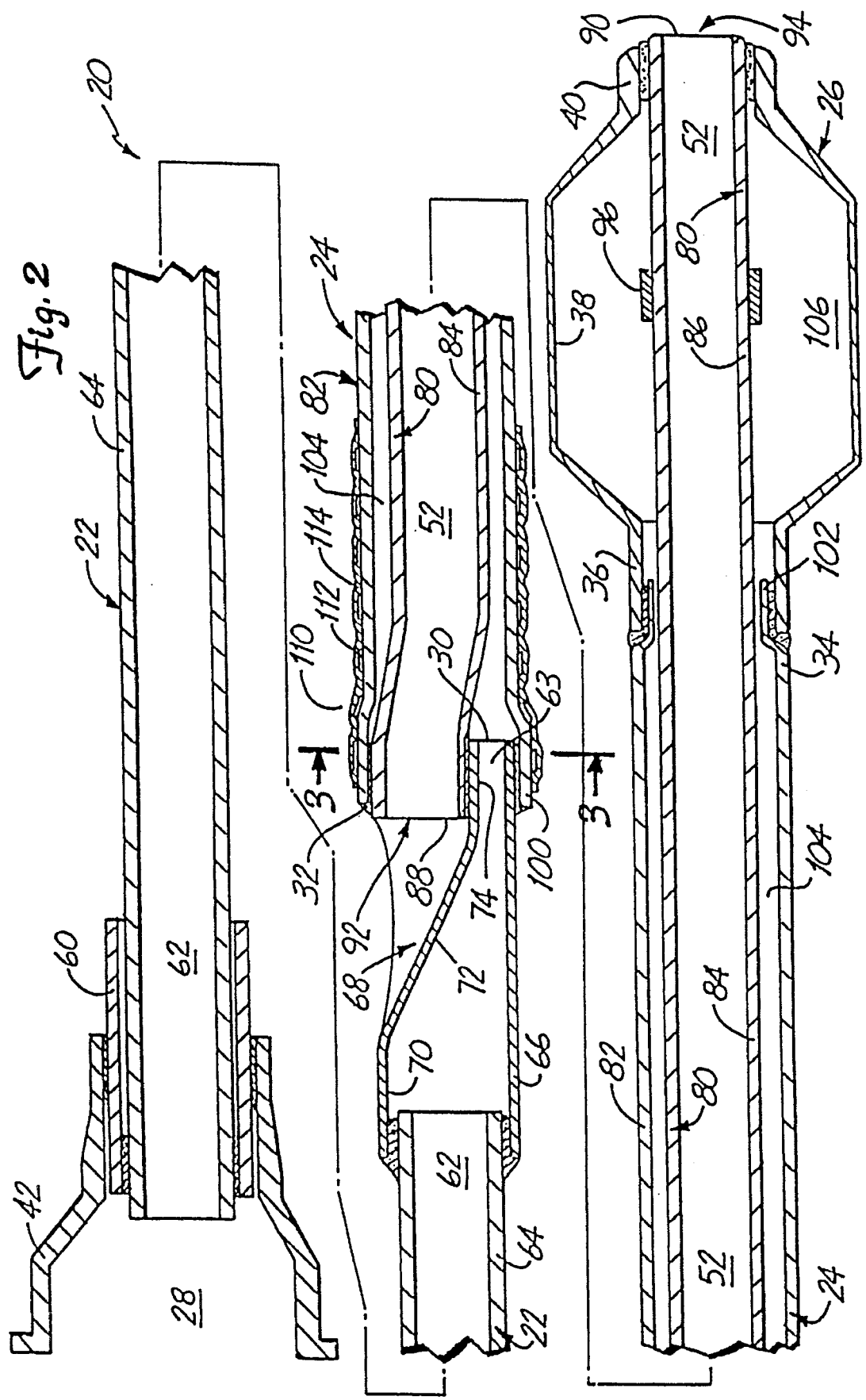

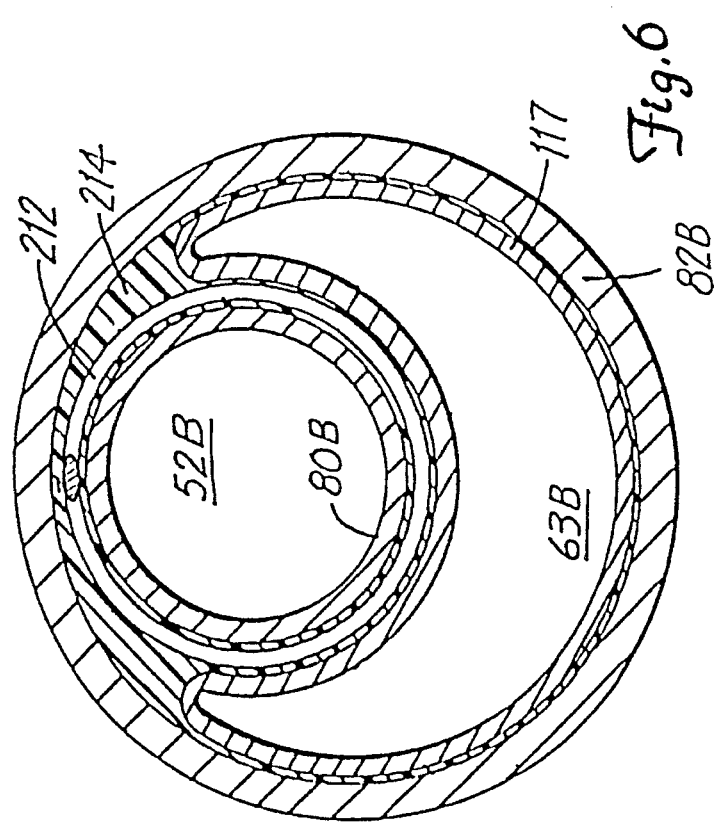
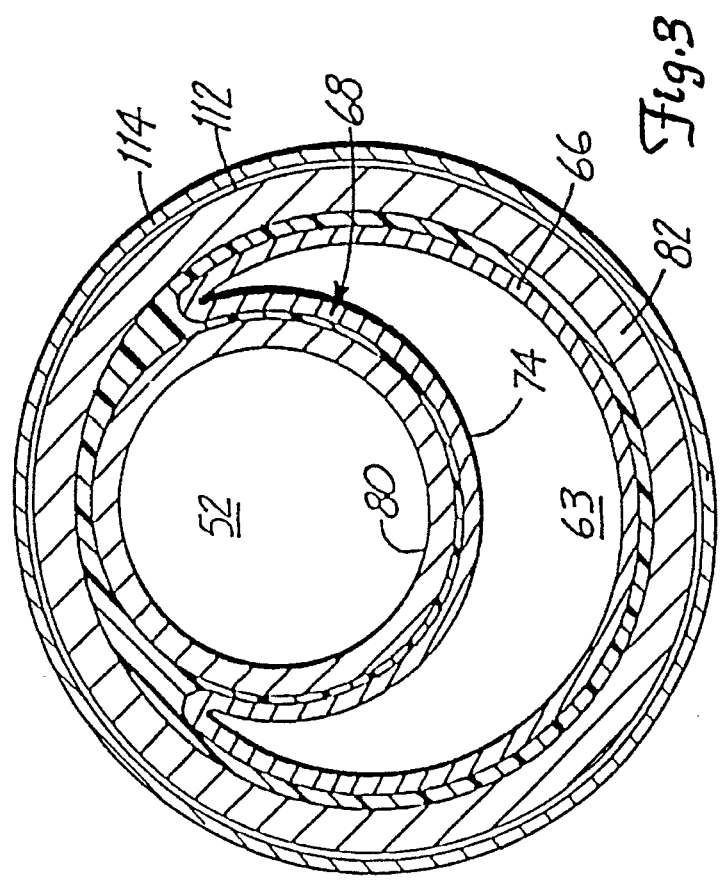

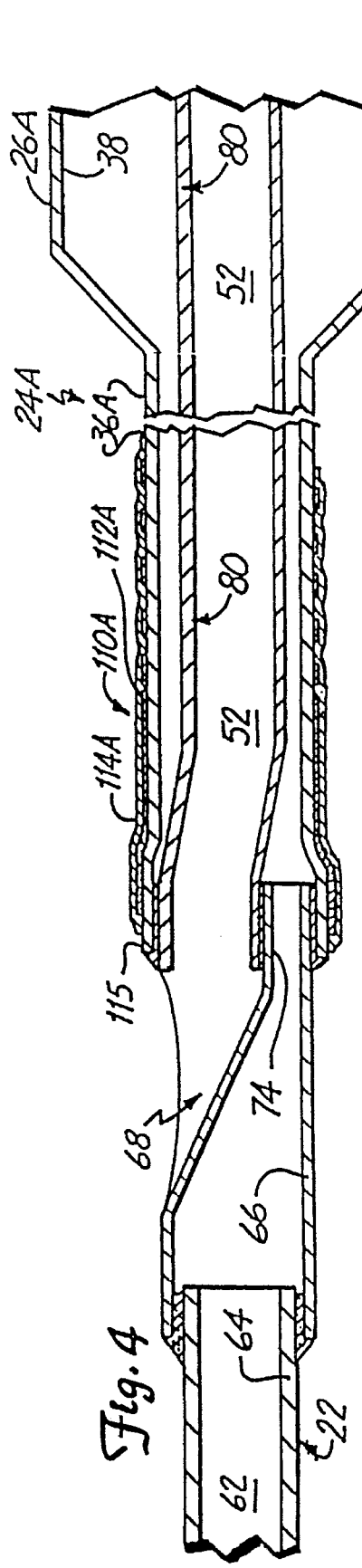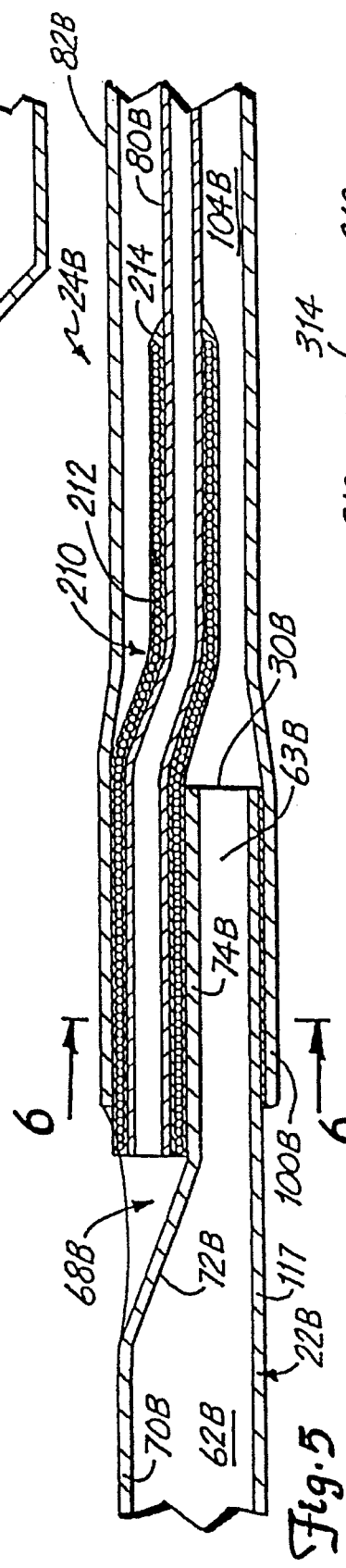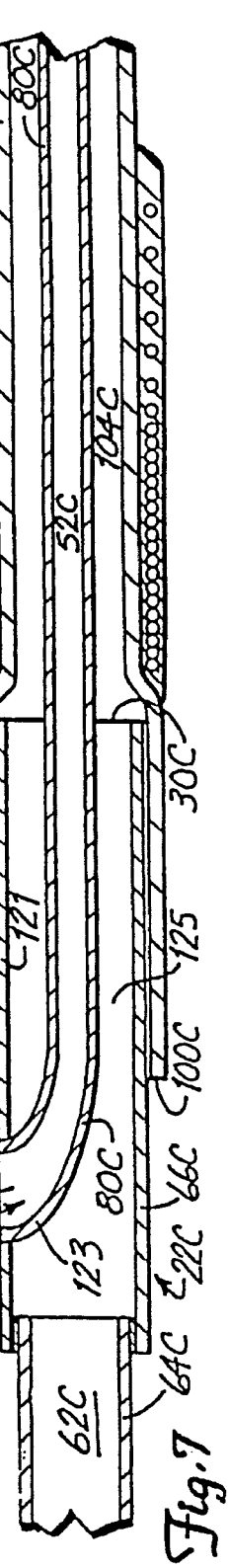

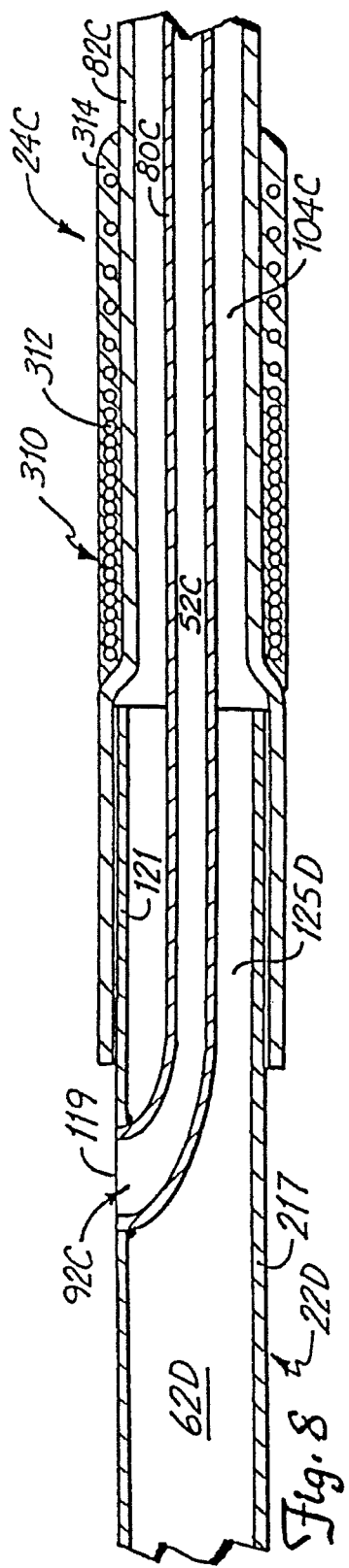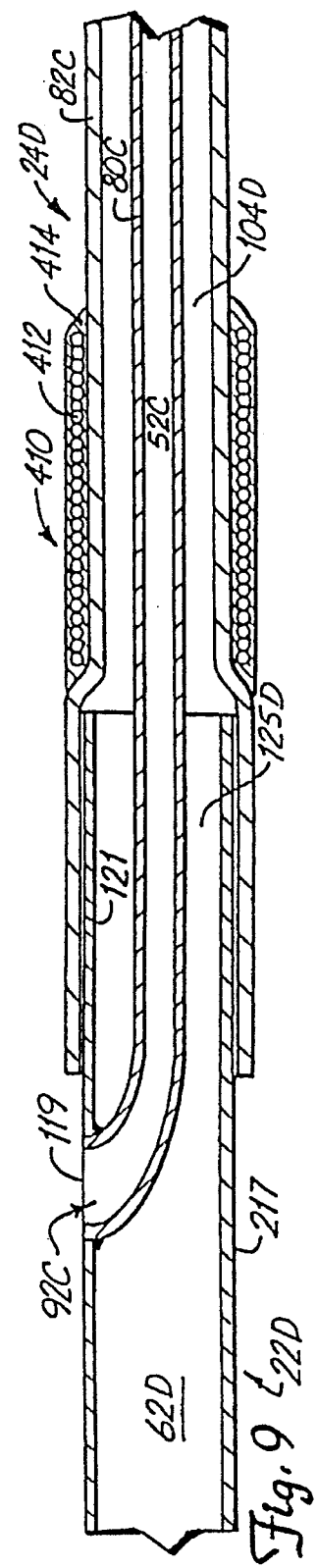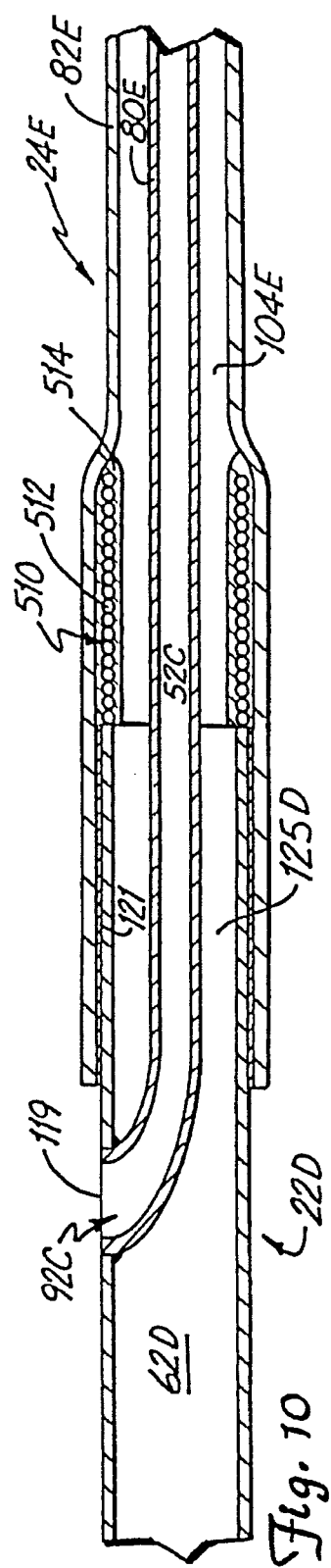

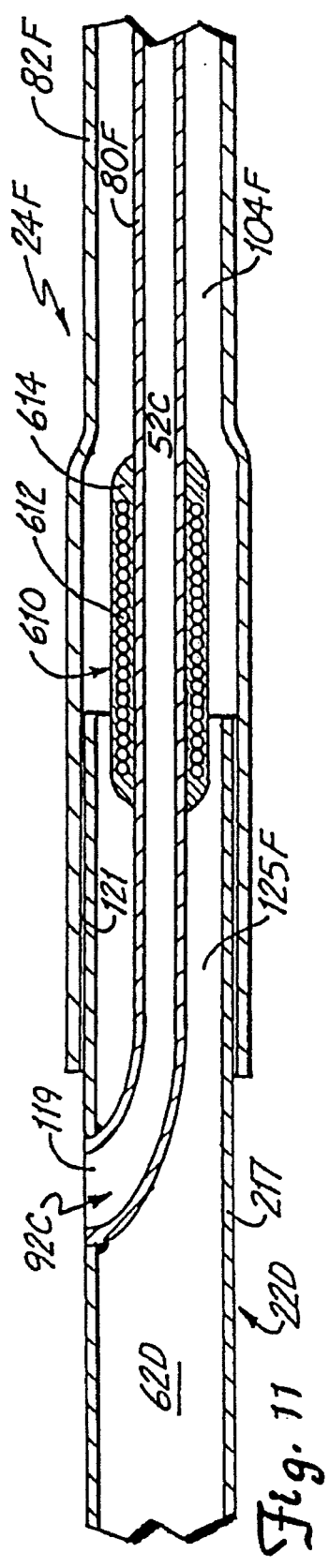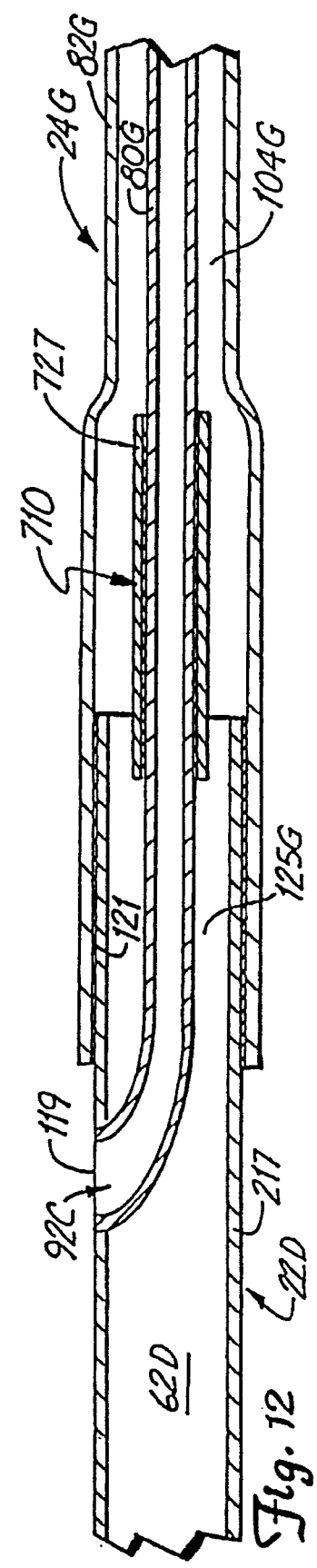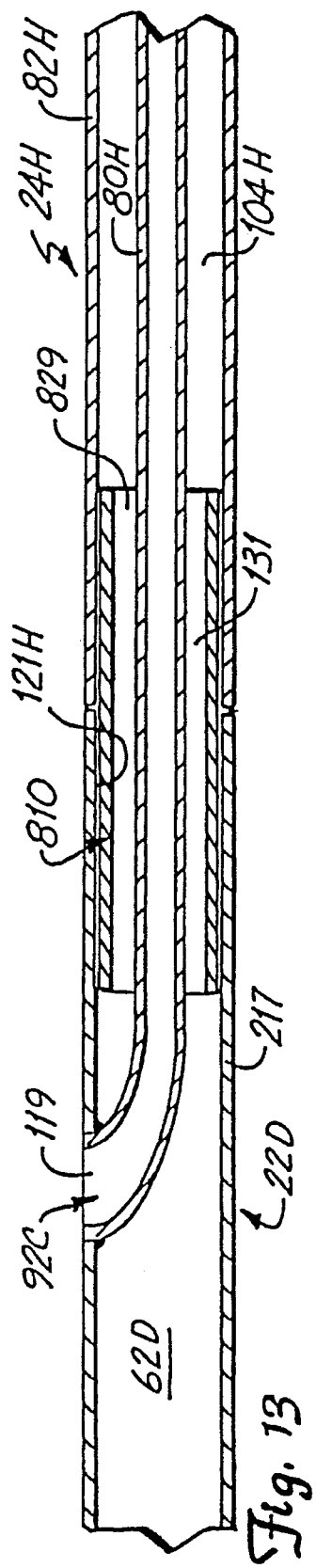

BALLOON CATHETER WITH DISTAL GUIDE WIRE LUMEN

RELATED APPLICATIONS

This application is a continuation of application Ser. No. 08/344,931, filed Nov. 23, 1994 (now abandoned), which is a continuation of application Ser. No. 08/035,254, filed Mar. 22, 1993, now U.S. Pat. No. 5,395,334, which is a continuation of application Ser. No. 07/792,786, filed Nov. 15, 1991, now U.S. Pat. No. 5,217,482, which is a continuation of application Ser. No. 07/574,265, filed Aug. 28, 1990, now U.S. Pat. No. 5,156,594.

BACKGROUND OF INVENTION

The present invention relates to the field of angioplasty. In particular, the present invention relates to a dilatation balloon catheter of the "over-the-wire" type having a relatively short distal guide wire lumen extending through the balloon of the catheter.

Angioplasty procedures have gained wide acceptance in recent years as efficient and effective methods for treating types of vascular disease. In particular, angioplasty is widely used for opening stenoses in the coronary arteries, although it is also used for the treatment of stenoses in other parts of the vascular system.

The most widely used form of angioplasty makes use of a dilatation catheter which has an inflatable balloon at its distal end. Typically, a hollow guide catheter is used in guiding the dilatation catheter through the vascular system to a position near the stenoses (e.g., to the coronary artery ostia). Using fluoroscopy, the physician guides the dilatation catheter the remaining distance through the vascular system until a balloon is positioned to cross the stenoses. The balloon is then inflated by supplying fluid under pressure through an inflation lumen in the catheter to the balloon. The inflation of the balloon causes stretching of the artery and pressing of the lesion into the artery wall, to reestablish acceptable blood flow through the artery.

There has been a continuing effort to reduce the profile and shaft size of the dilatation catheter so that the catheter not only can reach but also can cross a very tight stenosis. A successful dilatation catheter must also be sufficiently flexible to pass through tight curvatures, especially in the coronary arteries. A further requirement of a successful dilatation catheter is its "pushability". This involves the transmission of longitudinal forces along the catheter from its proximal end to its distal end so that a physician can push the catheter through the vascular system and the stenoses.

Two commonly used types of dilatation catheters are referred to as "over-the-wire" catheters and "non-over-the-wire" catheters. An over-the-wire catheter is one in which a separate guide wire lumen is provided in the catheter so that a guide wire can be used to establish the path through the stenoses. The dilatation catheter can then be advanced over the guide wire until the balloon on the catheter is positioned within the stenoses. One problem with the over-the-wire catheter is the requirement of a larger profile and a generally larger outer diameter along the entire length of the catheter in order to allow for a separate guide wire lumen therethrough.

A non-over-wire catheter acts as its own guide wire, and thus there is no need for a separate guide wire lumen. One advantage of a non-over-the-wire catheter is its potential for a reduced outer diameter along its main shaft since no discrete guide wire lumen is required. However, one disadvantage is the inability to maintain the position of the guide wire within the vascular system when removing the catheter and exchanging it for a catheter having a smaller (or larger) balloon diameter. Thus, to accomplish an exchange with a non-over-the-wire catheter, the path to the stenoses must be reestablished when replacing the catheter with one having a different balloon diameter.

In an effort to combine the advantages of an over-the-wire catheter with a non-over-the-wire catheter, catheters have been developed which have guide wire lumens which extend from a distal end of the catheter through the dilatation balloon and then exit the catheter at a point proximal of the dilatation balloon. The guide wire thus does not extend through the entire length of the catheter and no separate guide wire lumen is required along a substantially proximal section of the catheter. That proximal section can thus have a smaller outer diameter since it is only necessary to provide an inflation lumen therethrough for catheter operation. A further advantage of this type of modified over-the-wire catheter is that the frictional forces involved between the guide wire and the shortened guide wire lumen are reduced, thereby reducing resistance to catheter pushability and enhancing the "feel" and responsiveness of the catheter to a physician.

Perhaps the most significant advantage of using a shortened guide wire lumen is in the ease of exchange of the catheter over the guide wire. In performing an angioplasty procedure using such a catheter, the catheter is "back loaded" over the guide wire by inserting the proximal tip of the guide wire into a distal opening of the guide wire lumen in the catheter. The catheter is then advanced by "feeding" the catheter distally over the guide wire while holding the guide wire stationary. The proximal end of the guide wire will then emerge out of the proximal opening of the guide wire lumen (which is substantially spaced distally from the proximal end of the catheter itself) and is accessible again for gripping by the physician. The catheter can be preloaded onto the guide wire in this manner before the guide wire is inserted into the guide catheter or after. In either case, the guide wire is steered and passed through the guide catheter, coronary vessels and across a lesion. The exposed portion of the guide wire is then grasped while the catheter is advanced distally along the guide wire across the lesion. Using this procedure, little axial movement of the guide wire occurs during catheter loading and positioning for angioplasty.

If the dilatation balloon is found to be inadequate (too small or too large), the catheter can be similarly withdrawn without removing the guide wire from across the lesion. The guide wire is grasped while the catheter is withdrawn, and when the proximal opening of the guide wire lumen is reached, the grasping hand must be moved incrementally away from the proximal opening as the catheter is incrementally withdrawn, until the catheter is fully removed from the guide catheter and the guide wire is thus again exposed and accessible adjacent to the proximal end of the guide catheter.

This shortened guide wire lumen type of dilatation catheter design thus offers the advantages associated with the rapid exchangeability of catheters. The design also presents the potential to provide a smaller catheter shaft, since the guide wire is not contained within the proximal portion of the catheter shaft. The smaller catheter shaft thus allows for better contrast media injection and, as a result, better visualization. In addition, because of the rapid exchangeability features, standard non-extendable guide wires of approximately 175 centimeters in length may be used. Further, because the guide wire is contained in only a distal shorter guide wire lumen of the catheter, free wire movement is enhanced when compared to a standard over-the-wire catheter where the guide wire extends through a guide wire lumen extending along the entire length of the catheter.

While several structures for such shortened guide wire lumen dilatation catheter have been proposed these structures suffer from several disadvantages. Such catheters have been one piece polyethylene catheters having dual lumen configurations adjacent their distal regions. Typically, such catheters have larger than necessary shaft sizes and are stiffer in their distal regions than would be desired, including those portions bearing the dilatation balloon. A further disadvantage is that the proximal shaft portion of such catheters is relatively flexible, and has low column strength shaft, so that it tends to "bunch" and buckle when advanced across a lesion. To counteract this deficiency in such designs, additional stiffener elements have been provided in the shaft, which necessarily require a larger catheter shaft to accommodate the stiffener element structure. The known dilatation balloon catheter designs which include shortened guide wire lumens extending through the distal portion of the catheter suffer from the disadvantages mentioned above and do not take advantage of the unique opportunities presented by the possibilities of such designs in construction and application.

SUMMARY OF THE INVENTION

The present invention is an over-the-wire dilatation balloon catheter which has a guide wire lumen extending through only a distal portion of the catheter. The guide wire lumen extends from a distal end of the catheter proximally through a balloon of the catheter and exits the catheter at a point proximal of the balloon, but substantially distally from a proximal end of the catheter itself.

The present invention for a balloon dilatation catheter includes a thin-walled, high strength metallic tube having a longitudinal inflation lumen extending therethrough from its proximal end to its distal end. An intermediate sleeve section extends distally from the metallic tube. The sleeve section is more flexible than the metallic tube, and includes a proximal segment of inner core tube which has a longitudinal guide wire lumen extending therethrough and an outer sleeve which extends over the proximal segment of the core tube to define a longitudinally extending annular inflation lumen therebetween that is in fluid communication with the inflation lumen of the metallic tube. The guide wire lumen has an outlet at a proximal end of the proximal segment of the core tube, and the core tube has a distal segment which extends distally beyond the distal end of the outer sleeve. Means are provided for exposing the guide wire lumen outlet to the exterior of the catheter adjacent and proximal to the distal end of the metallic tube, without compromising the integrity of the inflation lumens extending through the catheter. An inflatable balloon extends over the distal segment of the core tube and has its proximal end connected to the distal end of the outer sleeve. A distal end of the balloon is connected to the core tube so that an interior of the balloon is in fluid communication with the annular inflation lumen in the sleeve section. Means are provided for preventing significant closure of the guide wire lumen and annular inflation lumen in the sleeve section adjacent the distal end of the metallic tube when the more flexible sleeve section is bent laterally relative to the metallic tube.

In a preferred embodiment of the present invention, the metallic tube is formed from a proximal relatively long stainless steel tube and a distal relatively short stainless steel tube bonded thereto. The outer diameter of the proximal tube is smaller than the outer diameter of the distal tube, thus providing a catheter structure which is highly trackable and has a generally small shaft outer diameter, yet is very pushable and responsive to a doctor controlling movement of the catheter from its proximal end. Preferably, the means for exposing includes a longitudinal crimp adjacent the distal end of the distal stainless steel tube. The crimp extends laterally inwardly from one side of the distal tube, and has a proximal transition region and distal bonding region. The proximal end of the inner core tube is nested within the distal bonding region of the crimp and bonded thereto. The outer sleeve extends over at least a distal portion of the bonding region and is sealably affixed thereabout.

The means for preventing closure of a present invention may take a number of different forms. In a preferred embodiment, the means for preventing closure comprises a coil member affixed to the sleeve section adjacent the distal end of the metallic tube. As such, the coil member may be affixed about the outer sleeve to extend distally from the metallic tube or about the inner core tube to extend distally from the metallic tube. Such a coil member further may have its coils spaced uniformly apart or spaced increasingly apart as it extends distally from the metallic tube. Preferably, the coil member is formed from a spirally shaped ribbon. A compression sheath is provided to envelope the coil member and maintain the coil member in secure engagement to the sleeve section. In an alternative embodiment, the means for preventing closure comprises a tubular member affixed to the sleeve section adjacent the distal end of the metallic tube, with the tubular member being formed from a polyimide material.

Such closure preventing means thus provide a bending relief design between the relatively stiff metallic tube and more flexible distal region of the balloon dilatation catheter, to prevent kinking during catheter preparation work and handling (prior to insertion of the dilatation catheter into the guide catheter and patient). Such kinking or "crimping" of the catheter can result in a binding on the guide wire as it extends through the guide wire lumen or a reduction in size of the annular inflation lumen between the metallic tube and balloon or a compromise in strength of the catheter tubings, all of which will compromise the utility and responsiveness of the dilatation catheter. In addition, the closure preventing means reduces the possibility of a failure or separation of the bonds adjacent the distal end of the metallic tube which may be caused by excess strain placed on such bonds during catheter preparation or handling.

BRIEF DESCRIPTION OF THE DRAWINGS

FIG. 2 is a sectional side elevational view of the balloon dilatation catheter of FIG. 1. FIG. 3 is an enlarged sectional view as taken along lines 3—3 in FIG. 2.

FIG. 4 is a sectional side elevational view of a portion of the catheter of the present invention, illustrating an alternative structure for a reinforcing coil member thereon.

FIG. 5 is a sectional side elevational view of a portion of the catheter of the present invention, illustrating an alternative structure for a reinforcing coil member thereon.

FIG. 6 is an enlarged sectional view as taken along lines 6—6 in FIG. 5.

FIG. 7 is a sectional view of a portion of an alternative embodiment of the catheter of the present invention.

FIG. 8 is a sectional view of a portion of an alternative embodiment of the catheter of the present invention.

FIG. 9 is a sectional view of a portion of an alternative embodiment of the catheter of the present invention.

FIG. 10 is a sectional view of a portion of an alternative embodiment of the catheter of the present invention.

FIG. 11 is a sectional view of a portion of an alternative embodiment of the catheter of the present invention.

FIG. 12 is a sectional view of a portion of an alternative embodiment of the catheter of the present invention.

FIG. 13 is a sectional view of a portion of an alternative embodiment of the catheter of the present invention.

Figure 1:
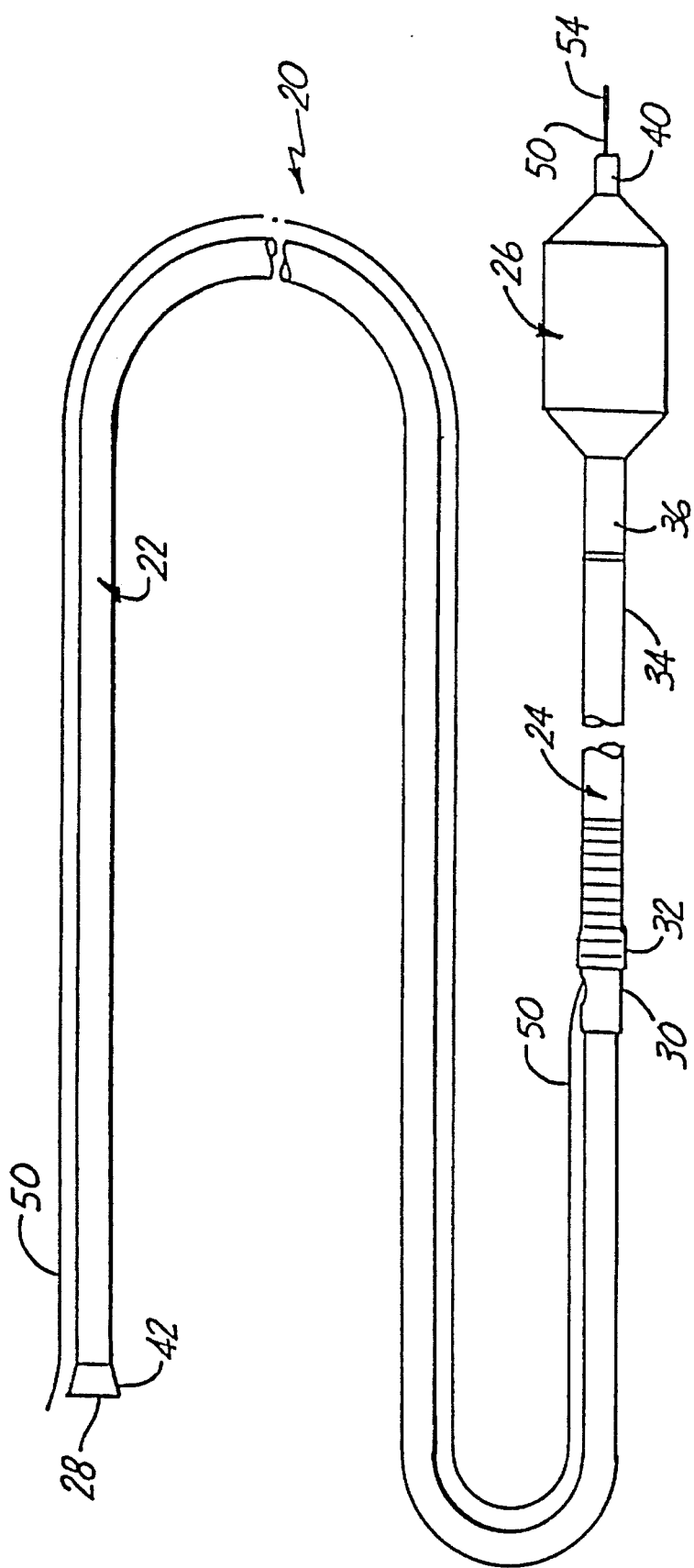
FIG. 1 is a side elevational view of a balloon dilatation catheter of the present invention having a distal guide wire lumen therethrough and showing a guide wire.

Although the above-identified drawing figures set forth various embodiments of the invention, other embodiments of the invention are also contemplated, as noted in the discussion. In all cases, this disclosure presents illustrated embodiments of the present invention by way of representation and not limitation. It should be understood that numerous other modifications and embodiments can be devised by those skilled in the art which will fall within the scope and spirit of the principles of this invention.

DETAILED DESCRIPTION OF THE PREFERRED EMBODIMENTS

Overall Catheter Structure

A balloon dilatation catheter 20 of the present invention is illustrated generally in FIG. 1. The catheter 20 has a proximal main shaft section 22, an intermediate sleeve section 24 and a distal balloon section 26. The main shaft section 22 has a proximal end 28 and a distal end 30. Likewise, the intermediate sleeve section 24 has a proximal end 32 and a distal end 34. The distal balloon section 26 has a proximal waist 36, an intermediate expandable segment 38 and a distal waist 40.

As illustrated in FIG. 1, the distal end 30 of the main shaft section 22 is connected to the proximal end 32 of the sleeve section 24, and the distal end 34 of the sleeve section 24 is connected to the proximal waist 36 of the balloon section 26. In use, the catheter 20 is coupled to an inflation device (not shown) by a luer manifold 42 connected to the proximal end 28 of the main shaft section 22. The inflation device thus provides or removes inflation solution from the catheter 20 to selectably inflate or deflate the intermediate expandable segment 38 of the distal balloon section 26 (in FIG. 1, expandable segment 38 is shown in its inflated configuration).

The catheter 20 of the present invention is designed for use in combination with a catheter guide element such as a guide wire 50. In use in a coronary application, both the guide wire 50 and the catheter 20 are fed through and guided to an arterial lesion by means of a tubular guide catheter (not shown). Both the catheter 20 and guide wire 50 are therefore longer than the guide catheter, with a typical catheter length of approximately 135 cm and a typical guide wire length of approximately 175 cm. As illustrated in FIG. 1, the guide wire 50 extends longitudinally along the exterior of the main shaft section 22 of the catheter 20. Adjacent the distal end 30 of the main shaft section 22, the guide wire 50 enters the structure of the catheter 20 and extends distally therethrough until it exits the catheter structure adjacent the distal waist 40 of the distal balloon segment 26. As seen FIG. 2, a separate guide wire lumen 52 is provided in the catheter 20 through the intermediate sleeve section 24 and distal balloon section 26 thereof. The guide wire 50 thus is only entrained within the catheter 20 within this guide wire lumen 52, which is much shorter than the total length of the catheter 20 (e.g., the guide wire lumen 52 is approximately 30 cm long). The guide wire 50 has a proximal end 53 and a distal end 54 and is of a typical structure for guiding angioplasty catheters. At its distal end 54, the guide wire 50 preferably has a coiled and rounded tip structure which is bendable for steerability of the guide wire.

Referring now to FIG. 2, which shows the catheter 20 in greater detail, it is seen that the proximal end 28 of the main shaft section 22 further has a strain relief tube 60 disposed between the luer manifold 42 and shaft section 22. The strain relief tube 60 is larger than the main shaft section 22, and thus provides a step-wise strain relief function between the inflexible luer manifold 42 and the more flexible main shaft section 22. The main shaft section 22, tubular member 60 and luer manifold 42 are secured together respectively by suitable adhesive means, such as epoxy or cyanoacrylate.

Main Shaft Section

The main shaft section 22 is preferably formed as a thin-walled, high strength stainless steel tube structure, which is referred to as hypodermic tubing or hypotube. As a tubular structure the main shaft section 22 thus has a longitudinally extending inflation lumen 62 extending therethrough from its proximal end 28 to its distal end 30, which provides a means for the movement and pressurization of inflation fluid through the catheter 20 to and from the distal balloon section 26.

In a preferred embodiment, the main shaft section 22 is formed from two stainless steel tube sections, a proximal relatively long shaft section 64 and a distal relatively short shaft section 66. A distal end of the proximal shaft section 64 and a proximal end of the distal shaft section 66 are sealably affixed together by suitable means, such as by a solder joint. The proximal end of the distal shaft section 66 fits coaxially over the distal end of the proximal shaft section 64, as seen in FIG. 2, thereby allowing the proximal shaft section 64 to assume a smaller outer diameter than the distal shaft section 66. The main shaft section 22 is provided with a lubricous coating (such as polytetraflouroethylene) to lessen frictional resistance (at least to the extent that the proximal shaft section 64 is so coated). The use of a thin-walled (e.g., 0.003 inch wall thickness), metallic tube structure for the main shaft section 22 thus provides a stiff enough shaft for pushability yet allows for a relatively small diameter shaft, thereby enhancing catheter visualization via fluoroscopy and catheter versatility. The inherent high strength nature of such a structure also allows it to withstand the fluid pressures necessary for proper catheter operation, which in a plastic shaft structure would require thicker walls. The high column strength and thickness of a hypotube shaft also gives improved responsiveness to the catheter. Thus, the balloon and distal regions of the catheter move definitively (in a 1:1 relationship) with motions imparted at the catheter's proximal end by a physician. This feature allows the physician to actually "sense" the pathway as the catheter is tracked, which gives valuable information in the passage of the catheter to and through the lesion.

In the distal shaft section 66 of the main shaft section 22, a longitudinal crimp 68 is provided which extends laterally inwardly from one side of the distal section 66. The distal shaft section 66 has three sections, a proximal tubular region 70, a transition region 72, and a distal bonding region 74. The crimp 68 extends from its proximal origin in the transition region 72 to its greatest lateral depth in the bonding region 74. The crimp 68, as further illustrated in FIG. 3, does not seal off or close the inflation lumen 62, but does transform the inflation lumen from a circular lumen 62 to a crescent shape through the bonding region 74, as seen at 63 in FIG. 3.

Catheter Intermediate Sleeve Section

The intermediate sleeve section 24 extends distally from the main shaft section 22, and is bonded thereto adjacent the bonding region 74 of the distal shaft section 66. The intermediate sleeve section 24 has two primary longitudinal components, an inner core tube 80 and an outer sleeve or tube 82. The inner core tube 80 has a proximal segment 84 within the sleeve section 24 and a distal segment 86 within the distal balloon section 26. The inner core tube 80 and outer sleeve 82 are both preferably formed from thin-walled high density polyethylene.

The inner core tube 80 has a proximal end 88 and a distal end 90. At its proximal end 88, the core tube 80 is nested within the bonding region 74 of the distal shaft section 66 and bonded thereto by suitable means, such as epoxy or cyanoacrylate. The core tube 80 is thus affixed to the main shaft section 22 in an "off-axis" alignment at the bonding region 74. However, as seen in FIG. 2, as the core tube 80 extends distally from the main shaft section 22, it is aligned generally coaxially with the shaft section 22.

The core tube 80 defines the guide wire lumen 52 extending through the catheter 20. The guide wire lumen thus has a proximal outlet 92 adjacent the proximal end of the core tube 80 and a distal outlet 94 adjacent the distal end 90 of the core tube 80. At least one marker band 96 is provided about the core tube 80 (preferably centered within the expandable segment 38 of the distal balloon section 26) to aid in illuminating the position of the catheter 20 via fluoroscopy during an angioplasty procedure.

The outer sleeve 82 is generally tubular in form, and has a proximal end 100 and a distal end 102. The outer sleeve 82 is bonded about the distal shaft section 66 and the core tube 80 adjacent the bonding region 74, as seen in FIGS. 2 and 3 and is held in place thereto by suitable means, such as epoxy or cyanoacrylate. The outer sleeve 82 extends distally from the main shaft section 22 over the proximal segment 84 of the core tube 80, and as such, defines a distal continuation of the inflation lumen of the catheter 20. A longitudinally extending annular inflation lumen 104 is formed between the core tube 80 and outer sleeve 82. Of course, the proximal end 100 of the outer sleeve 82 is securely sealed about the distal shaft section 66 and the core tube 80 so that the longitudinal inflation lumens 62 and 104 through the catheter 20 are not compromised to the exterior of catheter 20, but are in fluid communication therethrough.

The intermediate sleeve structure defined above is the basic sleeve structure for all embodiments of the present invention contemplated and disclosed herein—namely, an inner core tube bonded to a distal portion of the main catheter shaft, with an outer sleeve forming an annular continuation of the inflation lumen through the main shaft between the core tube and outer sleeve. As discussed below and illustrated herein, various configurations of the connections and components relative to the formation of the distal guide wire lumen, including the coupling of the main shaft to the intermediate sleeve section, are contemplated.

Catheter Distal Balloon Section

The distal balloon section 26 is connected to the components of the intermediate sleeve section 24. The proximal waist 36 of the balloon section 26 is connected to the distal end 102 of the outer sleeve 82 by suitable means, such as by epoxy or cyanoacrylate. The distal waist 40 of the balloon section 26 is bonded to the core tube 80 adjacent its distal end 90 by suitable means, such as by epoxy or cyanoacrylate. An interior 106 of the balloon section 26 is thus sealed and in fluid communication with the annular inflation lumen 104 within the sleeve section 24. In a preferred embodiment, the balloon section 26 is formed from a compliant balloon material (e.g., polyolefin), although a balloon formed from thin-walled non-compliant material (e.g., PET—polyethylene terephthalate) also contemplated.

Kink-resistant Structure

The metallic main shaft section 22 is relatively stiff compared to the polyethylene intermediate sleeve section 24. This creates a rather abrupt change in the flexibility of the materials for the catheter 20 adjacent the distal end 30 of the main shaft section 22 (at the bonding region 74). The use of a hypotube for the main shaft section 22 in the catheter 20 creates a catheter which is considerably stiffer than most previous over-the-wire angioplasty balloon catheter designs. Such stiffness is not a concern as long as the metallic main shaft section 22 remains in the relatively straight guide catheter within the patient, and indeed such stiffness provides distinct benefits in use of the catheter 20, as described above. In the distal portions of the catheter 20 (intermediate sleeve section 24 and distal balloon section 26), the catheter 20 must be very trackable and flexible in order to negotiate the tortuous coronary anatomy to and across the lesion. The relatively sharp transition in stiffness as the catheter structure changes from the metallic main shaft section 22 to the much more flexible polymer intermediate sleeve section 24 creates two concerns. First, during handling of the catheter prior to usage, there is a potential to kink the catheter structure at that flexibility transition point. Secondly, when the catheter is in vivo, the distal end 30 of the main shaft section 22 could potentially "dig in" to the guide catheter and create excessive friction due to the lack of bending support from the more flexible intermediate sleeve section 24.

To address these concerns, a kink-resistant structure 110 is provided to prevent kinking and possible damage to the intermediate sleeve section 24 during catheter preparation, handling and use. In its simplest form, this kink-resistant structure 110 provides a member of intermediate stiffness or transitory stiffness and kink-resistant nature between the relatively stiff main shaft section 22 and the relatively flexible intermediate sleeve section 24. The kink-resistant structure 110 includes a coil member 112 affixed to the intermediate sleeve section 24 adjacent the distal end 30 of the main shaft section 22. The coil member 112 creates an intermediate stiffener element between the relatively stiff main shaft section 22 and the relatively flexible intermediate sleeve section 24 to allow bending of the catheter without kinking. The coil member 112 preferably has its coils spaced uniformly apart, and is preferably formed from a spiral ribbon of stainless steel placed about the outer sleeve 82 along that portion thereof extending over the bonding region 74 and distally therefrom. The coil member 112 is secured to the outer sleeve 82 by suitable adhesive means, such as by epoxy. To further secure the coil member 112 to the intermediate sleeve section 24, a heat-shrinkable sheath 114 is fitted over the coil member 112. Preferably the sheath 114 is formed from a polyimide or polyolefin material which is expanded radially outwardly and then shrunk down over the coil member 112 and outer sleeve 82 to secure the coil member 112 thereto. To further secure the sheath 114 and coil member 112 in place, some adhesive is provided between the sheath 114 and the intermediate sleeve section 24. By covering the ends of the coil member 112, the sheath 114 also lessens the chances of those ends providing a rough edge or catch as the catheter 20 is advanced through the guide catheter or artery.

Although the kink-resistant structure is described and illustrated in connection with a balloon dilatation catheter, it is contemplated that such a structure be employed in any catheter shaft as a transition from a first thin-walled, high strength metallic tube structure to a second tube structure which is more flexible than the metallic tube structure. Such a kink-resistant structure, as described above (and also below in various embodiments), may be employed in a single lumen catheter shaft, or in multiple lumen catheter shaft having a central core tube such as the multi-lumen shaft illustrated by the intermediate sleeve section of the catheter disclosed in FIGS. 1–4.

Alternative Catheter Embodiment

Numerous alternative embodiments of the catheter of the present invention are contemplated. For example, several alternative arrangements for the main shaft section and intermediate sleeve structure portion of the catheter are illustrated and discussed herein, but it is not intended that the illustrated embodiments are all inclusive of those structures and designs which are included within the spirit and scope of the present invention. In the following discussion of further alternative embodiments of the present invention, to the extent a component is identical to that of a previously described embodiment, like reference numerals are used.

FIG. 4 illustrates an alternative embodiment for the distal portion of a catheter according to the present invention. Specifically, the outer sleeve (of the intermediate sleeve section) and the distal balloon section are formed from the same component, as a unitary member. Thus, proximal waist 36A of distal balloon section 26A is elongated proximally and acts as the outer sleeve for intermediate sleeve section 24A. A proximal end 115 of the proximal waist 36A is sealably fixed about the core tube 80 and main shaft section adjacent the bonding region 74 thereof. It should be understood that the prospect of having a unitary outer sleeve and balloon member is applicable to all embodiments disclosed herein and contemplated, although it is only illustrated and discussed with respect to the catheter structure of FIG. 4.

FIG. 4 also shows another variation for the catheter's structure illustrated in FIGS. 1–3. In FIG. 4, kink-resistant structure 110A includes coil member 112A which is defined as a spiral ribbon of stainless steel placed about a proximal portion of the proximal waist 36A along the bonding region 74 and distally therefrom. The coil member 112A does not have its coils uniformly spaced apart, but rather has its coils spaced increasingly further apart as the coil member extends distally from the main shaft section 22. This results in a coil member 112A which becomes increasingly more flexible, thereby "feathering out" the change in relative stiffness and strain or kink relief between the relatively inflexible main shaft section 22 and the relatively flexible intermediate sleeve section 24A. As before, a heat-shrinkable sheath 114A is fitted over the coil member 112A to further secure the coil member 112A to the sleeve section 24A.

In FIG. 5, a modified main shaft section 22B is illustrated. The main shaft section 22B is formed as a thin-walled, high strength stainless steel tube or hypotube, but is defined as a single tubular shaft 117 from its proximal end to its distal end 30B. The single shaft 117 has a longitudinally extending inflation lumen 62B therethrough, and at its proximal end (not shown) the single shaft 117 is mounted to an inflation device in a manner such as that illustrated for the catheter of FIG. 2. Adjacent its distal end 30B, the single shaft 117 has a longitudinal crimp 68B which extends laterally inwardly from one side of the single shaft 117. The single shaft 117 thus has three sections, a proximal, relatively elongated tubular region 70B, a relatively short distal transition region 72B and a relatively short distal bonding region 74B. The crimp 68B extends from its proximal origin in the transition region 72B to its greatest lateral depth in the bonding region 74B. The crimp 68B does not seal or close off the inflation lumen 62B, but rather transforms the inflation lumen 62B from a circular lumen to a half-moon lumen through the bonding region 74B, as seen at 63B in FIG. 6. It is again understood that the use of a single tube to define the main shaft section of the catheter of the present invention is applicable to the other alternative embodiments of the catheter structures disclosed herein.

FIGS. 5 and 6 also illustrate an alternative arrangement for the kink-resistant structure of the inventive catheter. Kink-resistant structure 210 includes coil member 212. The sleeve section 24B includes an outer sleeve 82B and an inner core tube 80B, with the core tube 80B adapted to be nested within and bonded to the main shaft section 22B in its distal bonding region 74B. The coil member 212 of the kink-resistant structure 210 is positioned about the core tube 80B within the distal bonding region 74B and extending distally therefrom. The coil member 212 is preferably formed from stainless steel (either from a wire or ribbon) and may have uniform coil spacing or increasingly spaced coils as the coil member 212 extends distally from the main shaft section 22B. The coil member 212 is secured to the core tube 80B by suitable means, such as by embedding the coil member 212 in an epoxy layer 214 about the core tube 80B. A proximal end 100B of the outer sleeve 82B is bonded about the main shaft section 22B and inner tube 80B and coil structure 210 in the bonding region 74B thereof, as seen in FIGS. 5 and 6. In the intermediate sleeve section 24B, the inner core tube 80B thus provides a guide wire lumen 52B therethrough, and an annular inflation lumen 104B is provided between the inner tube 80B and outer sleeve 82B. Although the kink-resistant structure 210 is within the annular inflation lumen 104 and the outer sleeve 82B necks down distally from the main shaft section 22B, the size of the annular inflating lumen 104 is sufficient to provide proper fluid flow to and from the catheter's balloon.

FIGS. 7–13 illustrate an alternative configuration for that portion of the catheter adjacent the proximal inlet of the guide wire lumen. Instead of providing a crimp structure in the distal end of the main shaft section, an aperture is provided adjacent to and proximal of the distal end of the main shaft section. The aperture is aligned and sealably coupled to the inner tube to define the guide wire lumen proximal outlet. In all disclosed embodiments, the main shaft section is preferably formed from a hypotube-like material.

As seen in FIG. 7, an alternative embodiment of the catheter of the present invention has a proximal main shaft section 22C formed from thin-walled, high strength stainless steel tubing. A longitudinally extending inflation lumen 62C extends therethrough from a proximal end of the main shaft section 22C to its distal end 30C. In the embodiment seen in FIG. 7, the main shaft 22C is formed from two stainless steel tube sections, a proximal relatively long shaft section 64C and a distal relatively short shaft section 66C bonded on the distal end of the proximal section 64C. This two-part main shaft section structure thus allows a substantial length of the main shaft section 22C to be formed from the proximal shaft section 64C which has a smaller diameter than the distal shaft section 66C.

The distal shaft section 66C has an oval-shaped aperture 119 extending through its wall, with the oval being elongated in the longitudinal direction of the main shaft section 22C. The aperture 119 is spaced proximally from a distal end of the distal shaft section 66C (the distal end 30C of the main shaft section 22C). The space between the aperture 119 and distal end 30C thus defines in part a bonding region 121 for connecting the main shaft section 22C to a distally extending intermediate sleeve section 24C.

As before, the intermediate sleeve section 24C includes an inner core tube 80C and an outer sleeve 82C. A proximal end 88C of the core tube 80C is sealably bonded about the aperture 119 to align the proximal end 88C and aperture 119 and thereby define a proximal outlet 92C for a guide wire lumen 52C extending through the core tube 80C. As seen in FIG. 7, a proximal portion 123 of the core tube 80C extends laterally from the aperture 119 into the distal shaft section 66C and turns longitudinally and distally relative thereto to be aligned generally coaxially therewith. As such, the inflation lumen 62C is continued distally past the aperture 119 as a generally annular inflation lumen 125, between the core tube 80C and distal shaft section 66C (along the bonding region 121). Proximal end 100C of the outer sleeve 82C is bonded about the distal shaft section 66C in the bonding region 121 by a suitable means, such as by epoxy or cyanoacrylate. As seen in FIG. 7, the outer sleeve 82C extends distally from the main shaft section 22C over the core tube 80C and defines a longitudinally extending annular inflation lumen 104C between the core tube 80C and outer sleeve 82C. The proximal end 100C of the outer sleeve 82C is sealed about the distal shaft section 66C so that the longitudinal inflation lumens 62C, 125 and 104C are not compromised to the exterior of the catheter, but are in fluid communication therethrough.

In FIG. 7, kink-resistant structure 310 includes coil member 312 (of a wire or ribbon-like structure) which is bonded about the outer sleeve 82C to extend distally from the distal end 30C of the main shaft section 22C. In this embodiment, the coil member 312 does not extend about any portion of the main shaft 22C. The coil member 312 is secured to the outer sleeve 82C by suitable adhesive means, such as epoxy 314, and is embedded therein to firmly hold the coil member 312 in place about the intermediate sleeve section 24C. In the embodiment of FIG. 7, the coil member 312 is illustrated with its coils being spaced increasingly longitudinally apart as the coil member 312 extends distally along the catheter.

FIGS. 8–13 also illustrate embodiments of the catheter of the present invention wherein an aperture is provided through the main shaft section wall accommodate the proximal outlet for the relatively short, distal guide wire lumen. As opposed to the embodiment of FIG. 7, however, the embodiments illustrated in FIGS. 8–13 show the main shaft section as a single shaft rather than as a multi-part shaft. Indeed, FIG. 8 illustrates a catheter structure identical to that of FIG. 7, except that the main shaft section 22D is shown as a single shaft 217, rather than having proximal and distal shaft sections 64C and 66C as seen in FIG. 7. As such, the catheter inflation lumen includes longitudinally extending inflation lumens 62D, 125D and 104D.

FIG. 9 is an embodiment of the catheter of the present invention otherwise similar to FIG. 8, except that kink-resistant structure 410 has coil member 412 with uniformly spaced coils along the entire length. Again, the entire coil member 412 is fixed to the outer sleeve 82C of the intermediate sleeve section 24C by embedding the coil member 412 within a suitable material such as epoxy or cyanoacrylate 414.

In the catheter structure of FIG. 10, intermediate section 24E has an inner core tube 80E and an outer sleeve 82E. The structure of the catheter is otherwise the same as the catheter of FIG. 9, except that the kink-resistant structure thereof is positioned inside the outer sleeve 82E rather than outside of the outer sleeve. Kink-resistant structure 510 is affixed to an inner surface of the outer sleeve 82E distally of the main shaft section 22D by a suitable means, such as embedded adhesive 514. The kink-resistant 510 includes coil member 512 which provides an intermediate stiffener between the relatively stiff main shaft section 22D and the relatively flexible intermediate sleeve section 24E. As seen, the outer sleeve 82E necks down distally from the kink-resistant structure 510 to provide a lower profile for the catheter in its distal regions. An annular inflation lumen 104E formed between the inner tube 80E and outer sleeve 82E (and at a proximal end thereof, between the inner tube 80E and the kink-resistant structure 510) is not compromised by such a necked-down sleeve design but maintained at sufficient size to provide for adequate and quick inflation and deflation of the balloon.

In FIG. 11 intermediate sleeve section 24F includes an inner core tube 80F and an outer sleeve 82F. Kink-resistant structure 610 is mounted about the inner tube 80F along the bonding region 121 and extending distally from the main shaft section 22D into the intermediate sleeve section 24F. The kink-resistant structure includes coil member 612 which is affixed about the core tube 80F by suitable means such as being embedded in epoxy or another suitable adhesive 614. As seen in FIG. 11, the outer sleeve 82F has an enlarged diameter at its proximal end to accommodate the main shaft section 22D and the kink-resistant structure 610, and so that the annular inflation lumens 125F and 104F about the core tube 80F remain sufficiently large to provide proper inflation and deflation pressures to the balloon of the catheter.

FIGS. 12 and 13 illustrate a further variation of the kink-resistant structure of the present invention. In the embodiments of FIGS. 12 and 13, the kink-resistant structure does not include a coil member, is formed from a polymer tube which is of intermediate stiffness between the main shaft section and intermediate sleeve section. In FIG. 12, kink-resistant structure 710 is provided which is formed from a polyimide or other stiff polymer tube 727. The tube 727 is bonded about an inner core tube 80G of the intermediate sleeve section 24G by a suitable adhesive, such as epoxy or cyanoacrylate. The tube 727 extends through a distal portion of the bonding region 121 and distally beyond the main shaft section 22D into the intermediate sleeve section 24G. Again, an outer sleeve 82G of the sleeve section 24G has an enlarged diameter at its proximal end to accommodate the main shaft section 22D and the kink-resistant structure 710, and so that the components are dimensioned such that annular inflation lumens 125G and 104G are not compromised.

In FIG. 13, kink-resistant structure 810 is illustrated, as formed from a polyimide or other stiff polymer tube 829 which is bonded to the inner surfaces of both the main shaft section 22D and an outer sleeve 82H of an intermediate sleeve section 24H at a bonding region 121H. The tube 829 thus provides not only a kink-resistant structure to accommodate the change in stiffness of the main shaft section and intermediate sleeve section, but also provides a substrate for bonding the two catheter sections together by a suitable adhesive, such as epoxy or cyanoacrylate. A core tube 80H of the sleeve section 24H extends through the interior of the tube 829 to the aperture 119 on the main shaft section 22D. Thus, an annular longitudinally extending inflation lumen 131 is formed as a "bridge lumen" (between the core tube 80H and tube 829) from the inflation lumen 62D to an annular inflation lumen 104H within the sleeve section 24H.

As mentioned above, various combinations of these alternative component and catheter structures are contemplated and are intended to be considered, although not explicitly shown. For example, it is contemplated that a two-part main shaft section structure (such as illustrated in FIGS. 2, 4 and 7) may be combined with any one of the kink-resistant structure such as that illustrated in FIGS. 8–13. By way of example and not limitation, a further example of such a combination may include the use of a distal balloon section having an elongated proximal waist (such as shown in FIG. 4) with any of the alternative kink-resistant structures disclosed herein.

Conclusion

The balloon dilatation catheter of the present invention is an over-the-wire catheter structure with a distal guide wire lumen which optimizes the features of such a catheter in a way not previously considered or achieved. The use of a hypotube-type main shaft for the catheter allows the attainment of a high strength, pushable shaft having thin walls and small diameter. The further use of a two-part hypotube shaft structure allows an even smaller diameter for the proximal elongated section of the main catheter shaft. Employing a crimp as a means for aligning and creating a proximal outlet for the relatively short guide wire lumen also serves to provide a transition region for exit of the guide wire from the catheter itself which is relatively gradual. The crimped shaft design also provides additional stiffness in the transition region where the guide wire enters and exits the catheter proximally of the balloon thereof, thereby creating a more rigorous catheter structure. Because the catheter of the present invention is based upon a relatively stiff proximal main shaft section, and such a catheter must have a relatively flexible distal portion for working through the tortuous arterial anatomy, a strain relief or kink-resistant structure is provided to make a more gradual transition between the relatively stiff main catheter shaft and the relatively flexible distal portion of the catheter. Various configurations of strain relief and kink-resistant structures are disclosed herein, and all are believed suitable to accomplish the desired end of preventing significant closure of the guide wire lumen and annular inflation lumen in the more flexible distal portions of the catheter, especially adjacent the distal end of the main catheter shaft.

Although the present invention has been described with reference to preferred embodiments, workers skilled in the art will recognize that changes may be made in form and detail without departing from the spirit and scope of the invention.

What is claimed is:

1. A catheter shaft assembly comprising:

a first thin-walled, high strength metallic tube structure having a lumen extending therethrough;

a second tube structure extending distally from the metallic tube, with the second tube structure being more flexible than the metallic tube structure and having a second lumen extending longitudinally therethrough which is in fluid communication with the first lumen;

a core tube disposed within the second tube and extending from proximate the proximal end of the second tube to a location distal the second tube, the core tube defining guidewire lumen having a proximal end and a distal end, and a guide wire lumen opening at each end of the guidewire lumen; and means for preventing significant closure of the second lumen, the means for preventing significant closure being adjacent a distal end of the metallic tube structure when the more flexible second tube structure is bent laterally relative to the metallic tube structure, wherein the means for preventing closure comprises a coil member affixed to the second tube structure adjacent the distal end of the metallic tube structure.

2. The catheter shaft assembly of claim 1, and further comprising:

an inner core tube extending coaxially through at least a portion of the first lumen and through the second lumen.

3. A balloon dilatation catheter comprising:

a thin-walled, high strength metallic tube having a longitudinal inflation lumen extending therethrough from its proximal end to its distal end;

an inner core tube having proximal and distal end and a longitudinal guidewire lumen extending therethrough, the proximal end of the core tube being disposed proximate the distal end of the metallic tube;

an intermediate sleeve section extending distally from the metallic tube, the sleeve section being more flexible than the metallic tube, and including an outer sleeve which extends over a proximal segment of the core tube to define an annular inflation lumen therebetween that is in fluid communication with the inflation lumen of the metallic tube, with the guide wire lumen having an outlet at a proximal end of the proximal segment of the core tube and an inlet at a distal end of the core tube, the core tube having a distal segment which extends distally beyond a distal end of the outer sleeve to the guidewire lumen inlet;

means for exposing the guide wire lumen outlet at the proximal end of the core tube to an exterior of the catheter without compromising the integrity of the inflation lumens extending through the catheter, the outlet being adjacent and proximal to the distal end of the metallic tube ;

an inflatable balloon extending over the distal segment of the core tube, the balloon having its proximal end connected to the distal end of the outer sleeve and having its distal end connected to the core tube so that an interior of the balloon is in fluid communication with the annular inflation lumen in the intermediate sleeve section; and means for preventing significant closure of the guide wire lumen and annular inflation lumen in the intermediate sleeve section, the means for preventing significant closure being adjacent the distal end of the metallic tube when the more flexible intermediate sleeve section is bent laterally relative to the metallic tube.

4. The balloon dilatation catheter of claim 3 wherein the means for preventing closure comprises a coil member affixed to the intermediate sleeve section adjacent the distal end of the metallic tube.

5. The balloon dilatation catheter of claim 4 wherein the coil member is affixed about the outer sleeve to extend distally from the metallic tube.

6. The balloon dilatation catheter of claim 5 wherein the coil member has its coils spaced increasingly apart as it ends distally from the metallic tube.

7. The balloon dilatation catheter of claim 3 wherein the metallic tube has an aperture therethrough at a point spaced proximally from its distal end, and wherein the proximal end of the inner tube is bonded to the metallic tube so that the outlet of the guide wire lumen is aligned with the aperture.

8. A balloon dilatation catheter comprising:

a first thin-walled, high strength, relatively inflexible tube having a longitudinal inflation lumen extending therethrough from its proximal end to its distal end, the first tube having, at the distal end thereof, a longitudinal crimp extending laterally inwardly from one side of the first tube with the crimp having a proximal transition region and a distal bonding region;

a second relatively flexible core tube having a longitudinal guide wire lumen extending therethrough from its proximal end to its distal end, with the proximal end of the second tube being nested within the distal bonding region of the longitudinal crimp of the first tube and bonded thereto so that the second tube extends distally from the first tube, the core tube defining a guidewire lumen outlet at the proximal end of the core tube and a guidewire lumen inlet at the distal end of the core tube; and a balloon assembly having an elongated proximal waist segment, an intermediate expandable segment and a distal waist segment, the proximal segment extending over at least a distal portion of the bonding region and sealably affixed thereabout so that the inflation lumen is in fluid communication with an interior of the balloon assembly through the proximal segment, with the balloon assembly extending distally from the bonding region over the second tube to a second bonding region where the distal waist segment is sealably affixed about the second tube.

9. The balloon dilatation catheter of claim 8, and further comprising:

means for preventing significant closure of the interior of the proximal waist segment of the balloon assembly, the means for preventing significant closure being adjacent the distal end of the first tube when the proximal waist segment is bent laterally relative to the first tube.

10. The balloon dilatation catheter of claim 9 wherein the means for preventing closure comprises a coil member affixed about at least a proximal portion of the proximal waist segment over and distally adjacent to the bonding region.

11. A balloon dilatation catheter comprising:

a first thin-walled, high strength, relatively inflexible tube having a longitudinal inflation lumen extending therethrough from its proximal end to its distal end, the first tube having, at the distal end thereof, a longitudinal crimp extending laterally inwardly from one side of the first tube with the crimp having a proximal transition region and a distal bonding region;

a second relatively flexible core tube having a longitudinal guide wire lumen extending therethrough from its proximal end to its distal end, with the proximal end of the second tube being nested within the distal bonding region of the longitudinal crimp of the first tube and bonded thereto so that the second tube extends distally from the first tube, the core tube defining a guidewire lumen outlet at the proximal end of the core tube and a guidewire lumen inlet at the distal end of the core tube;

a sleeve having a proximal end and a distal end, the sleeve proximal end being sealably affixed about the bonding region with the sleeve extending distally from the first tube and about the second tube to define a longitudinal annular inflation lumen between the sleeve and the second tube, and with the annular inflation lumen being in fluid communication with the inflation lumen in the fist tube;

a balloon having a proximal waist, an intermediate expandable segment and a distal waist, the proximal waist being sealably affixed to a distal end of the sleeve so that an interior of the balloon is in fluid communication with the annular inflation lumen, the balloon extending distally from its proximal end about the second tube and with the distal waist of the balloon sealably affixed about the distal end of the core tube; and means for preventing significant closure of the annular inflation lumen and guide wire lumen in a portion of the catheter just distally of the distal end of the first tube when that portion is bent laterally relative to the first tube, the means for preventing closure being disposed at the portion of the catheter bent laterally relative to the first tube.

* * * * *